United States Patent [19]

Van Der Puy et al.

[11] Patent Number: 5,777,184
[45] Date of Patent: Jul. 7, 1998

[54] PREPARATION OF FLUOROALKYL COMPOUNDS AND THEIR DERIVATIVES

[75] Inventors: Michael Van Der Puy, Amherst; Alagappan Thenappan, Cheektowaga, both of N.Y.

[73] Assignee: AlliedSignal Inc., Morristown, N.J.

[21] Appl. No.: 882,061

[22] Filed: Jun. 25, 1997

[51] Int. Cl.$^6$ .................................................. C07C 21/18
[52] U.S. Cl. .................. 570/135; 560/172; 568/484; 568/842
[58] Field of Search ............... 570/135; 560/172; 568/484, 842

[56] References Cited

U.S. PATENT DOCUMENTS

| | | | |
|---|---|---|---|
| 4,465,786 | 8/1984 | Zimmer et al. | 502/169 |
| 5,654,473 | 8/1997 | Van Der Puy | 560/262 |

*Primary Examiner*—Alan L. Rotman
*Assistant Examiner*—Garth M. Dahlen
*Attorney, Agent, or Firm*—Colleen D. Szuch; Jay P. Friedenson

[57] ABSTRACT

A process for producing a fluorinated olefin having the formula:

$$CH_{3-a}F_aCH=CHCl$$

where $a=1, 2$ or $3$, said process comprising catalytically reacting a chlorinated organic compound with a fluorination agent under conditions sufficient to form said hydrofluorocarbon compound, said chlorinated organic compound having the formula:

$$CH_bCl_cF_dCH_eCHCl_e$$

where $b=0, 1$ or $2$; $c=0, 1, 2,$ or $3$; $d=0, 1, 2$ or $3$; and $e=1$ or $2$ with the provisos that $b+c+d=3$, $c+e>1$ and $b+e<4$.

20 Claims, No Drawings

5,777,184

PREPARATION OF FLUOROALKYL COMPOUNDS AND THEIR DERIVATIVES

FIELD OF INVENTION

The present invention relates to fluoroalkyl compounds and their derivatives. More specifically, this invention relates to the preparation of a family of alkyl compounds having vinyl functionality and a methyl group with one or more fluorine atoms thereon. The vinyl functionality tends to be reactive and enables the formation of other useful fluorinated hydrocarbons such as fluorinated alcohols and fluorinated aldehydes.

BACKGROUND OF THE INVENTION

Fluoromethylated, functionalized compounds are useful in the preparation of more complex organic compounds. As used herein, the term "fluoromethylated" describes a compound having a methyl group with one or more fluorine atoms thereon. Among their other attributes, these compounds, particularly trifluoromethylated compounds, are known for imparting thermal and chemical resistance to polymers and for enhancing the effectiveness of agricultural products and pharmaceuticals. Examples of extensively used fluoromethylated compounds include trifluoroethanol, trifluoroacetic acid, trifluoroacetaldehyde, and trifluoroacetyl chloride and other low-molecular weight compounds. Higher-molecular weight fluoromethylated homologs of these compounds are not commercially available since preparations, which are convenient, economical, amenable to scale, and environmentally acceptable, have yet to be developed.

Known methods of producing higher weight fluoromethylated compounds such as trifluoropropanol and trifluoropropanal generally suffer from problems which make their commercial implementation impractical. For example, Henne et al. (A. L. Henne, R. L. Pelley, and R. M. Alm, 72 *J Am. Chem. Soc.*, 3370 (1950)) discusses the preparation of trifluoropropanol by oxidizing the Grignard reagent of $CF_3CH_2CH_2Cl$ with $O_2$ at $-78°$ C. The intermediate compound $CF_3CH_2CH_2Cl$, in turn, was prepared by the fluorination of $CCl_3CH_2CH_2Cl$. The reagent used in this process is highly flammable, thus rendering large-scale production extremely dangerous. B. T. Golding, P. J. Sellars, and W. P. Watson, 30 *J. Fluorine Chem.* 153 (1985) discloses the oxymercuration reaction of trifluoropropene to produce an organomercury compound, which, when reduced with sodium borohydride, produced $CF_3CH_2CH_2OC(O)CH_3$. Hydrolysis of the latter provided the desired trifluoropropanol. This process, however, involves the use of use of toxic mercury salts as stoichiometric reagents. Trifluoropropanal has been made by the oxidation of trifluoropropanol with sodium dichromate. Although Henne et al. reported a 57% yield for this reaction, Golding et al., using the same reagent, obtained the aldehyde in only 5.6% yield.

Alternative methods may be used to convert the corresponding acid, trifluoropropanoic acid, or its acid chloride, to either the alcohol or aldehyde (see, for example, R. Braden and E. Klauke, U.S. Pat. No. 4,420,433 (Dec. 13, 1983)). The methods for the preparation of the acid, however, generally suffer from the same difficulties noted above (see J-P. Bouillon, C. Maliverney, R. Merenyi and H. G. Viehe, 1 *J. Chem. Soc. Perkin Trans.* 2147 (1991) for a listing of available methods).

Therefore, a need exists for a process of preparing higher-weight, fluoromethylated compounds by means which avoid the aforementioned problems. The present invention fulfills this among other needs.

DESCRIPTION OF THE INVENTION AND PREFERRED EMBODIMENTS

The present invention provides for the synthesis of a family of conveniently-functionalized, fluoroalkyl compounds that can be readily converted, without the use of heavy-metal salts, into useful fluoromethylated compounds. The fluoroalkyl compounds are synthesized by one or more catalytic reactions from a readily available or readily synthesized starting material. In turn, these fluoroalkyl compounds, with their vinyl functionality, can be reacted with other materials to form a host of other useful fluoromethylated chemical compounds such as fluoro-alcohols and fluoroaldehydes.

One aspect of the invention comprises a process for preparing a fluoromethylated vinyl chloride having the formula:

$$CH_{3-a}F_aCH=CHCl \qquad (1)$$

where a=1,2 or 3, and preferably where a=3. In one embodiment, the fluoromethylated vinyl chloride is formed by catalytically reacting a fluorination agent with a starting material having the formula:

$$CH_bCl_cF_dCH_eCHCl_e \qquad (2)$$

where b=0, 1 or 2; c=0, 1, 2, or 3; d=0, 1, 2 or 3; e=1 or 2; with the provisos that b+c+d=3, c+e>1, and b+e<4, and preferably where b=0 and d<3, and more preferably where b=0, c=3, d=0, and e=2.

Catalytically reacting the starting material under conditions suitable to form the fluoromethylated vinyl chloride of Formula (1) represents a significant departure from the prior art. It is known that fluorination of a chlorinated hydrocarbon having the formula $CF_yCl_{3-y}CH_2CHF_wCl_{2-w}$, where w=0 or 1, and y=0, 1, 2 or 3 with $HF/SbCl_5$ provides $CF_3CH_2CHF_2$ in high yield (M. Van Der Puy and A. Thenappan, U.S. Pat. No. 5,574,192, assigned to the assignee of the present application). However, it has been found surprisingly that, when the reaction is conducted in the presence of certain catalysts, $CF_3CH=CHCl$ is the major volatile product, and $CF_3CH_2CHF_2$ is virtually absent. Suitable catalysts include, for example, tin tetrachlorides, titanium tetrachloride and mixtures thereof.

Another aspect of the invention comprises the identification of a fluoromethylated vinyl acetate compound and a method of preparing it from the fluoromethylated vinyl chloride of Formula (1). In a preferred embodiment, the fluoromethylated vinyl acetate compound has the formula:

$$CH_{3-f}F_fCH=CHOC(O)CH_3 \qquad (3)$$

where f=1, 2 or 3, and preferably where f=3.

Converting the vinyl chloride olefin of Formula (1) to the vinyl acetate olefin of Formula (3) also represents a significant departure from the prior art. The conversion of vinyl chlorides to vinyl acetates is known for non-fluorinated olefins. For example, in C. F. Kohll and R. Van Helden, *Rec. Trav. Chim. Pays-Bas*, 87 (1968) 481, a process is described which utilizes sodium acetate as the reagent and is catalyzed by divalent palladium salts such as $PdCl_2$ and $Pd(OAc)_2$. This disclosure, however, only considers non-fluorinated olefins. Olefins bearing fluorinated groups, particularly perfluoroalkyl groups, tend to be less reactive than their non-fluorinated analogs. For example, $CF_3CCL_3$ can be added easily to hydrocarbon olefins such as 1-butene using a copper-based catalyst, but no such addition occurs for $CF_3CH=CH_2$ under the same conditions (M. Van der Puy, 61 *J. Fluorine Chem.* 133 (1993). It has been found, however, that the floromethylated vinyl chloride may be catalytically reacted with a NaOAc/HOAc to produce the fluoromethylated vinyl acetate compound.

Yet another aspect of the invention comprises using the fluoromethylated vinyl acetate compound of Formula (3) as a common intermediate to produce other functionalized, fluoromethylated compounds such as fluoro-alcohols or fluoroaldehydes. In a preferred embodiment, a fluoroalcohol has the formula:

$$CH_{3-g}F_gCH_2CH_2OH \qquad (4)$$

where g=1,2 or 3, and preferably where g=3, and a fluoroaldehyde has the formula:

$$CH_{3-h}F_hCH_2CHO \qquad (5)$$

wherein h=1,2 or 3, and preferably where h=3.

Suitable starting materials of Formula (2) comprise aliphatic compounds having at least one terminal chlorinated methyl group. As mentioned above, such compounds are known in the art and are available readily or synthesized readily. According to Formula (2) suitable starting materials include, for example, $CCl_3CH_2CHCl_2$, $CFCl_2CH_2CHCl_2$, $CF_2ClCH_2CHCl_2$, $CF_3CH_2CHCl_2$, $CHCl_2CH_2CHCl_2$, $CHFClCH_2CHCl_2$, $CCl_3CH=CHCl$, $CFCl_2CH=CHCl$, $CF_2ClCH=CHCl$, $CHCl_2CH=CHCl$, $CH_2ClCH=CHCl$, and $CHFClCH=CHCl$. In a preferred embodiment, b=0 and d<3, which includes, for example, $CCl_3CH_2CHCl_2$, $CFCl_2CH_2CHCl_2$, $CF_2ClCH_2CHCl_2$, $CCl_3CH=CHCl$, $CFCl_2CH=CHCl$, $CF_2ClCH=CHCl$. In a more preferred embodiment, b=0, c=3, d=0, and e=1, which corresponds to $CCl_3CH_2CHCl_2$.

The starting materials of Formula (2) may be prepared by any means known in the art (see, for example, B. Boutevin et al., Monofunctional Vinyl Chloride Telomers. I. Synthesis and Characterization of Vinyl Chloride Telomer Standards, 18 Eur. Polym. J. 675 (1982) in 97 Chemical Abstracts 182966c (1982); Kotora et al., Selective Additions of Polyhalogenated Compounds to Chloro Substituted Ethenes Catalyzed by a Copper Complex, 44(2) React. Kinet. Catal. Lett. 415 (1991); and Examples 1 and 2 below). When $CCl_3CH_2CHCl_2$ is the starting material, it is preferably prepared by adding $CCl_4$ to vinylidene chloride in a telomerization process. The materials required for this process are readily available and relatively inexpensive. Alternatively, $CCl_3CH_2CHCl_2$ may be prepared by the reduction of $CCl_3CH_2CCl_3$ as well as by photochlorination of $CCl_3CH_2CH_2Cl$. Such processes are well known in the art and described, for example, in U.S. Patent No. 5,574,192.

A suitable fluorination agent includes any material capable of providing fluorine in the reaction. A preferred fluorination agent is substantially anhydrous hydrogen fluoride (HF). The presence of water in the reaction tends to deactivate the fluorination catalyst. The term "substantially anhydrous", as used herein, means that the HF contains less than about 0.05 weight % water and preferably contains less than about 0.02 weight % water. It should be understood, however, that the presence of water in the catalyst can be compensated for by increasing the amount of catalyst used.

Based on reaction stoichiometry, the required mole ratio of the fluorination agent to the chlorinated hydrocarbon is equal to the number of chlorine atoms to be replaced in the starting material. For example, if $CCl_3CH_2CHCl_2$ is used as the starting material and HF is used as the fluorination agent, then a stoichiometric molar ratio of HF to $CCl_3CH_2CHCl_2$ of 3 is needed theoretically. However, during the course of the reaction, some HF is normally removed inadvertently along with by-product HCl when limiting reactor pressure, and, thus, a stoichiometric excess of fluorination agent is desirable. In the preferred embodiment, multiples of the stoichiometric amount range from about 1 to about 15 and most preferably from about 1.5 to about 5.

As mentioned above, suitable catalysts for use in the present invention include tin tetrachlorides, titanium tetrachloride and mixtures thereof. The preferred catalyst, which gives a high selectivity for $CF_3CH=CHCl$, is $SnCl_4$. In the preferred embodiment, the catalyst is present in an amount, based on the mole percent of starting material, ranging from about 2% to about 80%, and preferably from about 5% to about 50%, and more preferably from about 10% to about 20%. Fluorination catalysts having a purity of at least 98% are preferred.

To commence the reaction, the starting material, fluorination agent and the catalyst are added to a reactor. The reactor according to the present invention may be any suitable fluorination reaction pressure vessel or autoclave, but preferably should be constructed from materials which are resistant to the corrosive effects of HF. Examples of such materials are Hastalloy-C, Inconel, Monel, and stainless steel 316. Such liquid phase fluorination reactors are well known in the art.

The starting material of Formula (2) and the fluorination agent are reacted in the presence of the catalyst under conditions sufficient to form the fluorinated olefin of Formula (1). The reaction may involve fluorination when b≧1 in Formula (2), dehydrochlorination when d=3, or a combination of the two when b≧1 and d<3. The reaction conditions such as temperature, pressures and contact times will vary. One of ordinary skill in the art, however, can optimize readily these conditions to obtain the desired results.

The temperature at which the reaction is conducted and the period of reaction will depend on the starting materials, amounts used, and catalyst used. Generally, reaction temperatures range from about 50° C. to about 200° C., and more preferably from about 90° C. to about 150° C.

Reaction times are dependent on several factors including, for example, catalyst concentration, the type of catalyst, and the temperature. Under preferred conditions, typical reaction time ranges from about 1 to about 25 hours, and under more preferred conditions, reaction time ranges from about 2 to about 8 hours.

The pressure of the reaction is not critical and varies depending on, for example, the quantity of fluorination agent used and the amount of hydrogen chloride generated. Convenient operating pressures range from about 50 to about 600 psig, and preferably from 50 to about 400 psig. Pressure may be adjusted by continuously removing hydrogen chloride and volatile products from the reactor by distillation.

The fluoromethylated vinyl chloride of Formula (1) provides convenient functionality to form other useful compounds such as fluoro-alcohols and fluoro-aldehydes. To this end, it is preferable first to convert the vinyl chloride group to a vinyl acetate group.

Converting the vinyl chloride group to the vinyl acetate group is performed by catalytically reacting the fluoromethylated vinyl chloride of Formula (1) with NaOAc/HOAc to produce the fluoromethylated vinyl acetate compound of Formula (3). In a preferred embodiment, the olefin $CF_3CH=CHCl$ is reacted with NaOAc/HOAc in the presence of $PdCl_2$ to provide $CF_3CH=CHOAc$ in good yield and at an acceptable rate. The temperature should be kept below 80° C. since above this temperature, $PdCl_2$ is converted to catalytically inactive metallic palladium. Preferred reaction temperatures range from about 50 to about 80° C., and more preferably from about 65 to about 75° C. Preferable solvents include, for example, dimethylformamide and acetic acid, the latter being preferred from a cost perspective. The catalyst Pd(O) can be regenerated by means known in the art.

To prepare the fluoro-alcohol of Formula (4), the fluoromethylated vinyl acetate compound of Formula (3) is preferably reduced first and then hydrolyzed. For example, the vinyl acetate $F_3CH=CHOC(O)CH_3$ may be reduced to $CF_3CH_2CH_2OC(O)CH_3$, and then hydrolyzed to form $CF_3CH_2CH_2OH$ in yields of 96% or more. A procedure for the hydrolysis of $CF_3CH_2CH_2OC(O)CH_3$ to the alcohol can be found in Golding et al. Although solvents such as lower molecular weight alcohols may be used in batch hydrogenations, it has been found that the reduction can be performed more conveniently without solvent. The catalyst, of the type commonly used for the hydrogenation of olefins (0.5 to 10% by weight Pd, Pt, or Rh on inert supports such as carbon and alumina) is suspended in $CF_3CH=CHOC(O)CH_3$. Hydrogen pressures need be only about 1 to about 10 atmospheres. Preferred temperatures range from about 50° C. to about 150° C. Generally, the reaction times range from about 4 to about 24 hours. Completion of reaction is evident when hydrogen uptake ceases. At this point, the catalyst preferably is recovered for recycle by any convenient means such as filtration. As is generally known to those in the art, the hydrogenation reaction described herein is also amenable to a vapor phase process.

To prepare an aldehyde of Formula (5), the vinyl acetate compound of Formula (3) is hydrolyzed. When the vinyl acetate compound is $CF_3CH=CHOC(O)CH_3$, for example, a particularly simple method involves heating the insoluble acetate with aqueous sulfuric acid until the mixture is homogeneous. The aldehyde $CF_3CH_2CHO$ may then be distilled directly from the aqueous solution. At reflux temperatures of about 100° C., about 1 to about 2 hours is sufficient to hydrolyze the acetate. Sulfuric acid is one of several strong acids which may be used to catalyze the hydrolysis, but sulfuric acid is quite inexpensive. Other acceptable acids include methanesulfonic acid, toluenesulfonic acid, trifluoromethanesulfonic acid, and perchloric acid. Preferred acid catalysts are relatively non-volatile compared to the product. Suitable acid concentrations range from about 1 to about 90%, and more preferably from about 5 to about 25%. In certain applications it may be preferable to remove all the moisture from the aldehyde. To this end, it can be dried by redistillation over $P_2O_5$ or other suitable drying medium.

The following examples are illustrative of the practice of the present invention.

EXAMPLES

Example 1.

This example illustrates the preparation of 1-chloro-3,3,3-trifluoropropene from 1-chloro-3,3,3-trichloropropane.

A 2-gallon Hastelloy autoclave (equipped with a stirrer and condenser at −5° C.) was charged with 3.00 Kg (13.9 mol) $CCl_3CH_2CHCl_2$, 1.33 Kg (66.5 mol) HF, and 524 g (2 mol) $SnCl_4$ and the mixture heated to 135° C. Pressure in excess of ca. 450 psi was bled off into a KOH scrubber which was connected to a calcium sulfate drier and two dry-ice traps in series. HCl generation subsided in approximately 4 hr. The reaction temperature was maintained for an additional hour prior to venting the volatile products to the cold traps. A total of 630 g crude product was obtained which consisted of 95% pure E/Z-$CF_3CH=CHCl$ (isomer ratio 26:1) for a yield of 35%. Distillation provided the major isomer in 97% purity, bp 20.5°–21.5° C. (lit. [R. N. Hazeldine, *J. Chem. Soc.*, 1952, 3490] bp 21° C.). $^1H$ NMR: δ6.94 (1 H, dq, J=13.5 and 2 Hz), 6.10 (1 H, dq, J=13.5 and 6.1 Hz). $^{19}F$ NMR: δ− 64.2 (dd, J=6.1 and 2 Hz). From the autoclave there was also obtained 1237 g of a mixture of pentachloropropane, tetrachlorofluoropropanes and trichlorodifluoropropanes.

Example 2.

This example illustrates the preparation of 3,3,3-trifluoropropenyl acetate from 1-chloro-3,3,3-trifluoropropene.

A glass pressure bottle was charged with 0.878 g (0.0049 mol) $PdCl_2$, 15.0 g (0.183 mol) NaOAc and 120 mL glacial acetic acid. The mixture was degassed, charged with 20.2 g (0.155 mol) $CF_3CH=CHCl$ and heated to 80° C. for 4 hours. The cooled mixture was then filtered and the filtrate diluted with 480 mL water. The product was extracted with 3×35 mL $CH_2Cl_2$, and the combined $CH_2Cl_2$ extracts were washed with 2×50 mL water, and dried ($Na_2SO_2$). Distillation gave 17.0 g (0.110 mol) of E/Z-$CF_3CH=CHOAc$ (71% yield), bp 105°–106° C. $^1H$ NMR (major isomer): 7.9 (dq, 1 H, $^3J_{H-H}$=12.6 Hz), 5.6 (m, 1 H), 2.1 (s, 3 H). $^{19}F$ NMR: −62.1 (major isomer); −59.1 (minor isomer). FT-IR: 1783.7; 1692.7 cm$^{-1}$.

Example 3.

This example illustrates the preparation of 3,3,3-trifluoropropyl acetate from 3,3,3-trifluoropropenyl acetate.

3,3,3-Trifluoropropenyl acetate (7.1. g) was hydrogenated in a glass pressure bottle overnight at 65°–70° C. using 0.1 g 10% Pd/C as catalyst and a maximum $H_2$ pressure of 35 psi. The catalyst was separated by centrifugation, providing 6.7 g of 97% pure $CF_3CH_2CH_2OAc$ (93% yield). Bp 112°–113° C. [lit. 112° C.; B. T. Golding, P. J. Sellars, and W. P. Watson, *J. Fluorine Chem.*, 30 (1985) 153]. $^1H$ NMR: δ4.29 (t, 2 H, J=6.4 Hz), 2.4 (m, 2 H), 2.07 (s, 3H). $^{19}F$ NMR: δ−65.8 (t, J=10.4 Hz).

Example 4.

This example illustrates the preparation of 3,3,3-Trifluoropropanal from 3,3,3-Trifluoropropyl acetate.

A mixture of 15 mL water, 3 g concentrated $H_2SO_4$, and 3.07 g of $CF_3CH=CHOAc$ was refluxed for about 1 hour, until the mixture became homogeneous. The reflux condenser was then replaced with a distillation column and still head. Trifluoropropanal, $CF_3CH_2CHO$, was distilled out slowly, up to a head temperature of 60° C. The product, 1.79 g (80% yield) was 99% pure by GC analysis. It was redistilled from $P_2O_5$, bp 55°–56° C. (lit. 56.0°–56.5° C. [A. L. Henne, R. L. Pelley, and R. M. Alm, *J. Am. Chem. Soc.*, 72 (1950) 370]). 2,4-Dinitrophenylhydrazone: mp 149.5°–150.5° C. (lit. mp 150.2°–150.8° C. [ibid]). FT-IR: 1740.4 cm$^{-1}$ (C=O).

What is claimed is:

1. A process for producing a fluoromethylated vinyl chloride compound having the formula:

where a=1,2 or 3, said process comprising:
   catalytically reacting a starting material with a fluorination agent under conditions sufficient to form said fluoromethylated vinyl chloride compound, said starting material having the formula:

$$CH_bCl_cF_dCH_eCHCl_e$$

where b=0, 1 or 2; c=0, 1, 2, or 3; d=0, 1, 2 or 3; and e=1 or 2 with the provisos that b+c+d=3, c+e>1, and b+e<4.

2. The process of claim 1, wherein the reaction is conducted in the presence of a catalyst selected from the group consisting of tin tetrachloride, titanium tetrachloride, and mixtures thereof.

3. The process of claim 2, wherein said catalyst is tin tetrachloride.

4. The process of claim 1, wherein a=3, b=0, and d<3.

5. The process of claim 4, wherein c=3, d=0, and e=2.

6. The process of claim 1, further comprising:

converting a vinyl chloride group of said fluoromethylated vinyl chloride compound to a vinyl acetate group to form a fluoromethylated vinyl acetate compound having the formula:

$$CH_{3-f}F_fCH=CHOC(O)CH_3$$

where f=1, 2 or 3.

7. The process of claim 6, wherein f=3.

8. The process of claim 6, further comprising:

reacting said fluoromethylated vinyl acetate compound to form an alcohol having the formula:

$$CH_{3-g}F_gCH_2CH_2OH$$

where g=1,2 or 3.

9. The process of claim 8, wherein g=3.

10. The process of claim 6, further comprising:

reacting said fluoromethylated vinyl acetate compound to form an aldehyde having the formula:

$$CH_{3-h}F_hCH_2CHO$$

wherein h=1,2 or 3.

11. The process of claim 10, wherein h=3.

12. A compound having the formula:

$$CH_{3-f}F_fCH=CHOC(O)CH_3$$

where f=1, 2 or 3.

13. The compound of claim 12, wherein f=3.

14. A process for producing a functionalized fluorinated compound having the formula:

$$CH_{3-i}F_iCH_jCH_kX$$

where i=1,2 or 3, j=1 or 2, k=1 or 2; and X=OH, O, or OC(O)CH₃ with the provisos that j=2 when X=OH or O; j=1 when X=OC(O)CH₃; k=1 when X=O or OC(O)CH₃, and k=2 when X=OH, said process comprising:

catalytically reacting a starting material having the formula:

$$CH_bCl_cF_dCH_eCHCl_e$$

where b=0, 1 or 2; c=1, 2, or 3; d=0, 1, 2 or 3; and e=1 or 2 with the provisos that b+c+d=3, c+e>1 and b+e<4, to form a fluoromethylated vinyl chloride; and converting said fluoromethylated vinyl chloride to said functionalized fluorinated compound.

15. The process of claim 14, wherein X is OC(O)CH₃ and said functionalized fluorinated compound is a fluoromethylated vinyl acetate; and wherein converting said fluoromethylated vinyl chloride to said functionalized fluorinated compound comprises:

catalytically reacting said fluoromethylated vinyl chloride with NaOAc/HOAc to produce said fluoromethylated vinyl acetate.

16. The process of claim 14, wherein X is OH and said functionalized fluorinated compound is an alcohol; and wherein converting said fluoromethylated vinyl chloride to said functionalized fluorinated compound comprises:

converting said fluoromethylated vinyl chloride to a fluoromethylated vinyl acetate; and converting said fluoromethylated vinyl acetate to said alcohol.

17. The process of claim 14, wherein said functionalized fluoromethylated compound is an aldehyde wherein X is O and wherein converting said vinyl chloride to said hydrofluorocarbon comprises:

converting said fluoromethylated vinyl chloride to a fluoromethylated vinyl acetate;

converting said fluoromethylated vinyl acetate to said aldehyde.

18. A process for producing a fluoromethylated, functionalized compound having the formula:

$$CH_{3-i}F_iCH_jCH_kX$$

where i=1,2 or 3, j=1 or 2, k=1 or 2; and X=OH, O, or OC(O)CH₃ with the provisos that j=2 when X=OH or O; j=1 when X=OC(O)CH₃; k=1 when X=O or OC(O)CH₃, and k=2 when X=OH, said process comprising:

converting a fluoromethylated vinyl chloride compound having the formula:

$$CH_{3-a}F_aCH=CHCl$$

where a=1,2 or 3 to said fluoromethylated, functionalized compound.

19. The process of claim 18, wherein X is OC(O)CH₃ and said fluoromethylated, functionalized compound is a fluoromethylated vinyl acetate; and wherein converting said fluoromethylated vinyl chloride to said fluoromethylated, functionalized compound comprises:

catalytically reacting said fluoromethylated vinyl chloride with NaOAc/HOAc to produce said fluoromethylated vinyl acetate.

20. The process of claim 18 wherein converting said fluoromethylated vinyl chloride to said fluoromethylated, functionalized compound comprises:

catalytically reacting said fluoromethylated vinyl chloride with NaOAc/HOAc to produce said fluoromethylated vinyl acetate; and converting said fluoromethylated vinyl acetate to a fluoromethylated, functionalized compound selected from the group consisting of fluoro-alcohol wherein X=OH and a fluoro-aldehyde wherein X=O.

* * * * *

UNITED STATES PATENT AND TRADEMARK OFFICE
CERTIFICATE OF CORRECTION

PATENT NO. : 5,777,184
DATED : July 7, 1998
INVENTOR(S) : Van Der Puy, et. al.

It is certified that error appears in the above-identified patent and that said Letters Patent is hereby corrected as shown below:

Column 6, line 57, delete "370" and substitute -- 3370 -- therefor.

Claim, 14, line 11, "c=1, 2, or 3" should read -- c=0, 1, 2, or 3 --.

Signed and Sealed this

Thirtieth Day of November, 1999

Attest:

Attesting Officer

Q. TODD DICKINSON

Acting Commissioner of Patents and Trademarks